United States Patent [19]

Röckseisen

[11] Patent Number: 5,675,625
[45] Date of Patent: Oct. 7, 1997

[54] APPARATUS FOR POSITIONING AND MARKING A PATIENT AT A DIAGNOSTIC APPARATUS

[75] Inventor: Armin Röckseisen, Scharnebeck, Germany

[73] Assignee: Lap GmbH Laser Applikationen, Luneburg, Germany

[21] Appl. No.: 488,729

[22] Filed: Jun. 8, 1995

[30]  Foreign Application Priority Data

Jun. 17, 1994 [DE] Germany .................. 44 21 316.6

[51] Int. Cl.$^6$ ............................................. A61B 6/08
[52] U.S. Cl. ................................. 378/206; 378/20
[58] Field of Search ............................ 378/206, 20

[56]  References Cited

U.S. PATENT DOCUMENTS

| | | | |
|---|---|---|---|
| 4,242,587 | 12/1980 | Lescrenier | 378/206 |
| 4,385,397 | 5/1983 | Verro | 378/206 |
| 4,538,289 | 8/1985 | Scheibengraber | 378/206 |

*Primary Examiner*—Craig E. Church
*Attorney, Agent, or Firm*—Vidas, Arrett & Steinkraus, P.A.

[57] ABSTRACT

An apparatus for positioning and marking a patient at a diagnostic apparatus, for example prior and after transillumination in a computer tomograph, comprising a plurality of line lasers which project lines in planes perpendicular to each other for alignment with a patient body zone to be irradiated and for marking thereof, the improvement of which comprises a first line laser being fixed to a support member which is mounted so as to be rotatable about an axis adapted to be aligned substantially to a central axis of the diagnostic apparatus, e.g. computer tomograph, the light beam of the eccentrically positioned line laser being in a plane extending through a Z-axis, which plane is perpendicular to the bed between said diagnostic apparatus and said support member when the support member is in a zero position, said support member being adapted to be driven by a numerically controlled drive and control means being provided for displacing said support member in response to control data corresponding to coordinates of a tumor determined by said diagnostic apparatus.

5 Claims, 1 Drawing Sheet

Fig.1
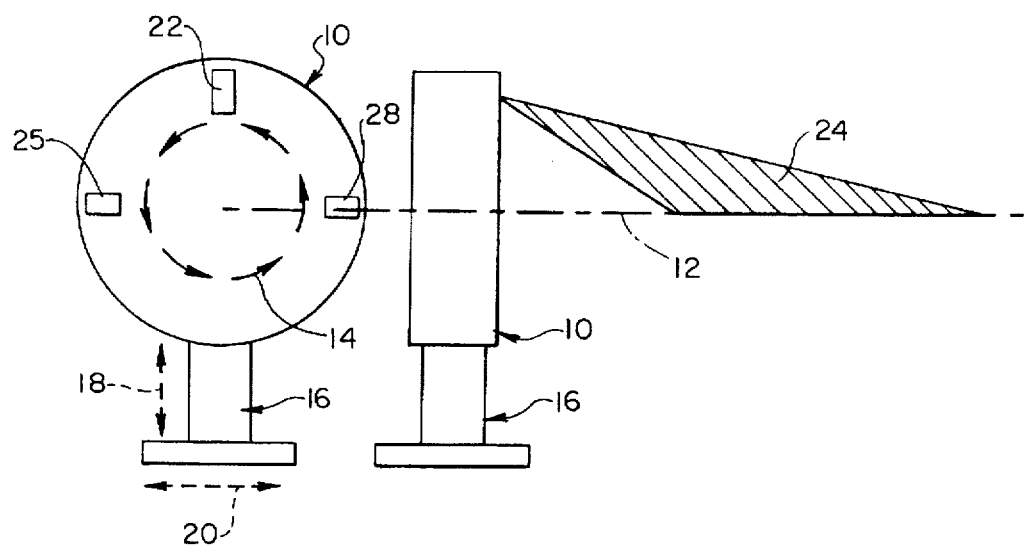
Fig.2
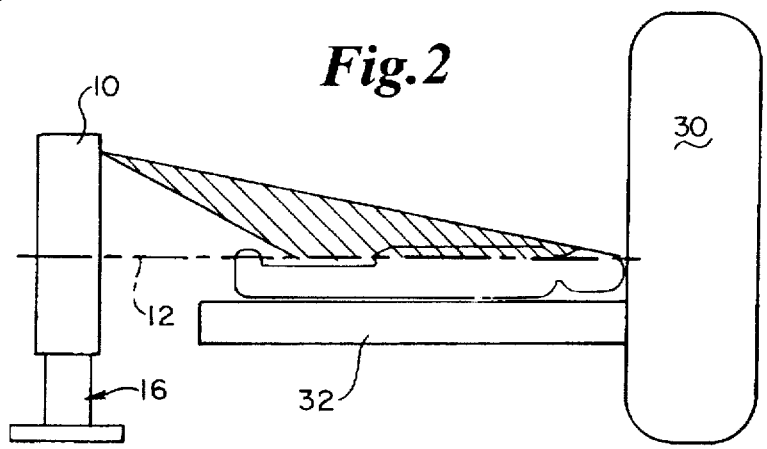
Fig. 3
|   |   |   |   |   |
|---|---|---|---|---|
| \multicolumn{4}{|l|}{−112} | X mm |
| \multicolumn{4}{|l|}{76} | Y |
| 7 | 8 | 9 |   | X |
| 4 | 5 | 6 |   |   |
| 1 | 2 | 3 |   | Y |
| − | 0 | + |   |   |

APPARATUS FOR POSITIONING AND MARKING A PATIENT AT A DIAGNOSTIC APPARATUS

The present invention relates to an apparatus for positioning and marking a patient at a diagnostic apparatus, for example prior and after having been transilluminated in a computer tomograph.

In radiation therapy it is necessary to direct the beam of the radiation source precisely onto the patient body zone to be irradiated, and this in a reproduceable manner. For reducing the strain on zones not to be treated the radiation source is pivoted about a so-called isocenter so that the center of the zone to be irradiated receives always the same treatment dosis while the adjacent zones not to be treated receive a substantially reduced treatment loading. Positioning of a patient with respect to the radiation apparatus is to be performed such that the center of the zone to be irradiated coincides with the isocenter of the radiation apparatus. The position of the zone to be irradiated may be determined by suitable diagnostic methods, for example by means of a computer tomograph (CT). The position of the zone to be irradiated is indicated on the patient body by marking the projection of the zone to be irradiated on the skin. By means of line laser systems fixedly arranged in the irradiation space the patient can be precisely positioned on a bed. By means of a sagittal line the patient can be aligned to the axis of rotation.

As mentioned above the coordinates of the zone to be irradiated may be determined by means of a computer tomograph. Therefore, it is necessary to mark the determined coordinates on the patient body so that the center of the tumor is in the isocenter of the radiation apparatus when the patient is being positioned.

It is an object of the present invention to provide an apparatus for positioning and marking a patient by means of a diagnostic apparatus such as a computer tomograph.

The invention has been defined in patent claim 1.

In the apparatus of the present invention the rotatable line laser projects a line onto the body of the patient which is to be diagnosed in a computer tomograph (CT). In a zero position this line is a sagittal line which is projected onto the patient centrally with respect to the Gantry of the CT in the direction of the latter. The support member of the laser can be comprised for example of a ring or a disk which is positioned perpendicularly to the axis of the CT. As a result the axis of rotation extends through the central axis of the CT. By rotating the support member the laser line may be projected onto the patient under any angle of rotation, and this along the longitudinal axis and always aligned to the axis of rotation (virtual isocenter). The rotational movements are obtained by a numerically controlled drive which is controlled by suitable control electronics.

By the above described positioning of the line laser the line generated by the latter is independent of the angular position at similar spacings from the patient body so that projection of identical lines as to their dimensions and brightness will result. By the input of control data for adjusting the support member said line may be displaced in accordance with the coordinates of the zone to be irradiated, which coordinates have been determined before by the CT. This allows to transfer the coordinates of tumors onto the outside of the body.

According to a further development of the invention the support member may be displaced laterally and/or in height by numerically controlled drives. This allows to align the axis of rotation of the support member and accordingly of the line lasers to the central axis of the zone to be irradiated.

A further development of the invention provides a pair of further line lasers fixed to said support member in diametrically opposed relationship and arranged to generate light planes which extend laterally on opposite sides of the patient body perpendicular to the light plane of said first laser and to intersect with the latter a virtual isocenter. Finally, it is possible to provide at least a third laser for generating a transversal line which has a predetermined spacing from the transverse axis of the CT. Preferably, said third laser is mounted so as to be displaceable along an axis parallel to the central axis and can be displaced by means of a suitable numerically controlled drive.

Before the start of the diagnosis the described system is in a zero condition. The line lasers on the support member project three lines, i.e. a sagittal line and a pair of lateral lines which intersect in the virtual isocenter. The third laser projects a transversal line which as mentioned has a predetermined spacing from the transverse axis of the CT. As a result the system when in the described zero position projects a similar cross of coordinates as in the above described fixedly mounted laser system.

By means of this line system the patient can be oriented before being moved to the Gantry of the CT by means of a displaceable bed. After the patient has been transilluminated or scanned, he/she will be moved—by means of a suitable drive which is controlled by the control of the CT—to a position where the zone to be irradiated is in the plane of the transversal line. This determines one coordinate for the marking to be performed. The other coordinates which also result from the diagnostic result of the CT are entered into the control electronics for the support member and the other lasers. This may be performed for example by means of a keyboard in order to predetermine the control data of the control means for the drives to provide for respective displacements of the lasers. The use of a manually operable keyboard is of advantage insofar as the system is independent of special CTs.

Rotating the support member allows to move the laser lines sequentially into the desired positions so that by means of the laser lines projected onto the patient body the coordinates of the zone to be irradiated as determined by the CT may be transferred onto the outside of the patient body so as to be marked thereon in order to provide for reproduceable positioning thereof with respect to the isocenter in radiation therapy.

Vertically and laterally displacing the rotating system allows, as mentioned above, to make the axis of rotation coincide with the central axis of the zone to be irradiated.

The invention will be explained in more detail with reference to the drawings.

FIG. 1 is a front and side view of a support member of a laser for the apparatus of the invention.

FIG. 2 is a side view of the apparatus in FIG. 1 with reference to a computer tomograph.

FIG. 3 is a keyboard for the apparatus in FIG. 1.

FIG. 1 shows a rotary member 10 adapted to be driven so as to rotate about an axis 12 by a not shown numerically controlled drive. This is indicated by the arrows 14. The support member 10 is mounted so as to be rotatable about the horizontal axis upon a post 16 which allows to displace the support member 10 both in a vertical direction as indicated by the double arrow 18 and in a horizontal direction as indicated by the double arrow 20.

A first line laser 22 is mounted to the support member 10 on a vertical diameter thereof in FIG. 1. The line laser 22 generates—when in the zero position as shown—a line on the axis 12 in a plane 24 which extends vertically through the axis 12. A pair of further diametrically opposite line lasers 26, 28 generate lines in a horizontal plane perpendicular to the plane 24, with the plane 24 being intersected in the axis 12.

As may be seen in FIG. 2, the axis 12 coincides with the axis of a computer tomograph (CT) which has been designated by 30. A patient to be diagnosed lies upon a bed 32. The bed 32 can be displaced horizontally into the Gantry of the CT by means of a numerically controlled drive which is controlled by control data of the CT.

In one position of the bed 32 before the CT 30 the patient can be oriented in accordance with the lines of the lasers 22, 26 and 28. Thereafter, the patient along with the bed 32 is moved into the computer tomograph. After the so-called scanning operation the bed 32 is moved therefrom by means of the control of the CT to a position such that the tumor is in a transversal plane which is generated by one or two line lasers in the space of the CT, with the light planes being perpendicular to the described light planes of the lasers 22, 26 and 28. The remaining X- and Y-coordinates which have been determined by the scanning operation are entered into a table according to FIG. 3. Thereafter not shown control means control the drives of the support member 10. By rotation thereof the desired positions of the lasers 22, 26 and 28 are obtained one after the other. By means of the laser lines projected onto the body in this manner the coordinates of the tumor as determined in the CT will be transferred onto the outside of the body of the patient and will be marked thereon in order to provide for reproduceable positioning with respect to the isocenter during irradiation of the patient.

Vertical and lateral displacements of the support member 10 allow to make the axis of rotation coincide with the central axis of the tumor.

I claim:

1. In a computerized tomography system including a gantry having a longitudinal axis, and rotatable scanner which rotates about said axis in a scan plane, and further including a table for support of a patient, said table being drivable along said longitudinal axis by suitable driving means between a first position outside of said gantry and a predetermined position inside said gantry relative to said can plane, the improvement comprising an apparatus for marking a patient for treatment with radiation means after the coordinate data of a tumor of a patient has been located by said computer tomograph, said marking apparatus comprising a support member located on an end of said table in said first position thereof opposite to said gantry, said support member including a driving means having a drive which rotates said support member about a horizontal axis and moves said support member in a vertical and/or horizontal direction, said driving means being controlled through a control means, said control means receiving data from a key pad into which data is entered from said computer tomograph, said control means converting said data from said key pad into control data to move said support member by said driving means, said support member supporting a first line laser generating a first beam in a plane through said horizontal axis and supporting a pair of second line lasers arranged in a diametrically opposed relationship which generate second beams in planes perpendicular to the plane of said first beam whereby the coordinates of the rumor are transferred to the exterior of the body of the patient for marking purposes.

2. An apparatus as defined in claim 1, wherein said control means key pad comprises a key-type input means for entry of the coordinates or control data determined by said computer tomograph.

3. An apparatus as defined in claim 1, wherein said control means is controlled by a machine control of said computer tomograph.

4. An apparatus as defined in claim 1, wherein said support member is arranged to be adjusted in height said driving means.

5. An apparatus as defined in claim 1, wherein said support member is arranged to be laterally displaceable said driving means.

* * * * *